(12) United States Patent
Ogdahl (10) Patent No.: US 9,017,382 B2
(45) Date of Patent: Apr. 28, 2015

(54) COLLAPSIBLE TISSUE ANCHOR DEVICE AND METHOD

(75) Inventor: Jason Westrum Ogdahl, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 664 days.

(21) Appl. No.: 12/468,754

(22) Filed: May 19, 2009

(65) Prior Publication Data

US 2009/0287229 A1 Nov. 19, 2009

Related U.S. Application Data

(60) Provisional application No. 61/054,202, filed on May 19, 2008.

(51) Int. Cl.
*A61B 17/04* (2006.01)
*A61F 2/00* (2006.01)
*A61B 17/00* (2006.01)

(52) U.S. Cl.
CPC ... *A61B 17/0401* (2013.01); *A61B 2017/00986* (2013.01); *A61B 2017/0409* (2013.01); *A61B 2017/0412* (2013.01); *A61B 2017/0414* (2013.01); *A61B 2017/0417* (2013.01); *A61B 2017/0438* (2013.01); *A61B 2017/0445* (2013.01); *A61B 2017/0448* (2013.01); *A61B 2017/0458* (2013.01); *A61B 2017/0464* (2013.01); *A61F 2/005* (2013.01)

(58) Field of Classification Search
USPC ......... 606/151, 185, 139, 148, 222, 232, 223, 606/224, 214, 218, 227, 225, 213, 329, 916, 606/215–217, 219, 74, 144, 300–303, 321, 606/326; 600/30, 37; 623/23.72; 411/34, 411/38, 42, 44–46, 74, 53–56, 57.1–60.1, 411/60.3, 76, 35, 21, 24, 25, 30, 51, 32, 411/80.5, 80.1, 80.2
See application file for complete search history.

(56) References Cited

U.S. PATENT DOCUMENTS 3,580,313 A 5/1971 McKnight
4,548,202 A 10/1985 Duncan
(Continued)

FOREIGN PATENT DOCUMENTS

| EP | 0643945 A2 | 7/1994 |
|---|---|---|
| EP | 0632999 A1 | 1/1995 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9730638 A1 | 8/1997 |
| WO | WO9747244 A1 | 12/1997 |
| WO | WO9819606 A1 | 5/1998 |

(Continued)

OTHER PUBLICATIONS

Capio™ CL—Transvaginal Suture Capturing Device—Transvaginal Suture Fixation to Cooper's Ligament for Sling Procedures, Boston Scientific, Microvasive®, 8 pages, (2002).

(Continued)

*Primary Examiner* — Jocelin Tanner
(74) *Attorney, Agent, or Firm* — Gregory L. Koeller (57) ABSTRACT

Collapsible tissue anchor device and method for inserting into a tissue structure in a first non-collapsed configuration and collapsing into a second collapsed configuration. A sleeve is provided having a bolt or shank extending through an interior. The bolt or shank exerts a force upon the sleeve to collapse it thereby forming flanges that engage or abut tissue. A sling, suture, mesh or the like may be coupled to a portion of the anchor to support tissue or an organ.

14 Claims, 5 Drawing Sheets

(56) References Cited

U.S. PATENT DOCUMENTS

| | | | |
|---|---|---|---|
| 4,632,100 A | 12/1986 | Somers et al. | |
| 4,708,553 A * | 11/1987 | Braychak et al. | 411/34 |
| 4,873,976 A | 10/1989 | Schreiber | |
| 4,938,760 A | 7/1990 | Burton et al. | |
| 4,969,892 A | 11/1990 | Burton et al. | |
| 4,979,956 A | 12/1990 | Silvestrini | |
| 5,013,316 A | 5/1991 | Goble et al. | |
| 5,019,032 A | 5/1991 | Robertson | |
| 5,085,661 A | 2/1992 | Moss | |
| 5,141,520 A | 8/1992 | Goble et al. | |
| 5,203,864 A | 4/1993 | Phillips | |
| 5,209,756 A | 5/1993 | Seedhom et al. | |
| 5,256,133 A | 10/1993 | Spitz | |
| 5,268,001 A | 12/1993 | Nicholson et al. | |
| 5,269,783 A | 12/1993 | Sander | |
| 5,328,077 A | 7/1994 | Lou | |
| 5,354,292 A | 10/1994 | Braeuer et al. | |
| 5,370,662 A | 12/1994 | Stone et al. | |
| 5,376,097 A | 12/1994 | Phillips | |
| 5,383,904 A | 1/1995 | Totakura et al. | |
| 5,480,403 A * | 1/1996 | Lee et al. | 606/232 |
| 5,520,700 A | 5/1996 | Beyar et al. | |
| 5,527,342 A | 6/1996 | Pietrzak et al. | |
| 5,544,664 A | 8/1996 | Benderev et al. | |
| 5,571,139 A | 11/1996 | Jenkins, Jr. | |
| 5,584,860 A | 12/1996 | Goble et al. | |
| 5,591,163 A | 1/1997 | Thompson | |
| 5,591,206 A | 1/1997 | Moufarrege | |
| 5,643,320 A | 7/1997 | Lower et al. | |
| 5,647,836 A | 7/1997 | Blake et al. | |
| 5,674,247 A | 10/1997 | Sohn | |
| 5,690,655 A | 11/1997 | Hart et al. | |
| 5,697,931 A | 12/1997 | Thompson | |
| 5,709,708 A | 1/1998 | Thal | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,754,412 A * | 5/1998 | Clavin | 361/804 |
| 5,782,862 A | 7/1998 | Bonuttie | |
| 5,807,403 A | 9/1998 | Beyar et al. | |
| 5,836,314 A | 11/1998 | Benderev et al. | |
| 5,842,478 A | 12/1998 | Benderev et al. | |
| 5,873,891 A | 2/1999 | Sohn | |
| 5,925,047 A | 7/1999 | Errico et al. | |
| 5,948,001 A * | 9/1999 | Larsen | 606/232 |
| 5,954,057 A | 9/1999 | Li | |
| 5,972,000 A | 10/1999 | Beyar et al. | |
| 5,980,558 A | 11/1999 | Wiley | |
| 5,984,927 A | 11/1999 | Wenstrom, Jr. | |
| 5,988,171 A | 11/1999 | Sohn et al. | |
| 5,997,554 A | 12/1999 | Thompson | |
| 6,007,539 A | 12/1999 | Kirsch et al. | |
| 6,019,768 A | 2/2000 | Wenstrom et al. | |
| 6,027,523 A | 2/2000 | Schmieding | |
| 6,036,701 A | 3/2000 | Rosenman | |
| 6,048,351 A | 4/2000 | Gordon et al. | |
| 6,053,935 A | 4/2000 | Brenneman et al. | |
| 6,099,552 A | 8/2000 | Adams | |
| 6,200,330 B1 | 3/2001 | Benderev et al. | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,319,272 B1 | 11/2001 | Brenneman | |
| 6,334,446 B1 | 1/2002 | Beyar | |
| 6,334,750 B1 * | 1/2002 | Hsieh | 411/508 |
| 6,334,865 B1 * | 1/2002 | Redmond et al. | 606/213 |
| 6,387,041 B1 | 5/2002 | Harari et al. | |
| 6,406,423 B1 | 6/2002 | Scetbon | |
| 6,406,480 B1 | 6/2002 | Beyar et al. | |
| 6,423,072 B1 | 7/2002 | Zappala | |
| 6,440,154 B2 | 8/2002 | gellman et al. | |
| 6,451,024 B1 | 9/2002 | Thompson et al. | |
| 6,454,778 B2 | 9/2002 | Kortenbach | |
| 6,506,190 B1 | 1/2003 | Walshe | |
| 6,544,273 B1 | 4/2003 | Harari et al. | |
| 6,582,443 B2 | 6/2003 | Cabak et al. | |
| 6,592,610 B2 | 7/2003 | Beyar | |
| 6,599,235 B2 | 7/2003 | Kovac | |
| 6,635,058 B2 | 10/2003 | Beyar et al. | |
| 6,673,010 B2 | 1/2004 | Skiba et al. | |
| 6,730,110 B1 | 5/2004 | Harari et al. | |
| 6,746,455 B2 | 6/2004 | Beyar et al. | |
| 6,908,473 B2 | 6/2005 | Skiba et al. | |
| 6,911,002 B2 | 6/2005 | Fierro | |
| 6,974,462 B2 | 12/2005 | Sater | |
| 6,981,983 B1 | 1/2006 | Rosenblatt et al. | |
| 7,144,415 B2 * | 12/2006 | Del Rio et al. | 606/232 |
| 7,297,102 B2 | 11/2007 | Smith et al. | |
| 7,326,213 B2 | 2/2008 | Benderev et al. | |
| 7,601,118 B2 | 10/2009 | Smith et al. | |
| 7,637,860 B2 | 12/2009 | MacLean | |
| 7,686,759 B2 | 3/2010 | Sater | |
| 7,740,576 B2 | 6/2010 | Hodroff | |
| 7,762,942 B2 | 7/2010 | Neisz et al. | |
| 7,789,821 B2 | 9/2010 | Browning | |
| 7,887,273 B2 * | 2/2011 | Vigliotti et al. | 411/38 |
| 2001/0027321 A1 | 10/2001 | Gellman et al. | |
| 2001/0041895 A1 | 11/2001 | Beyer et al. | |
| 2002/0035369 A1 | 3/2002 | Beyar et al. | |
| 2002/0050277 A1 | 5/2002 | Beyar | |
| 2002/0055748 A1 | 5/2002 | Gellman et al. | |
| 2002/0082619 A1 | 6/2002 | Cabak et al. | |
| 2002/0095064 A1 | 7/2002 | Beyar | |
| 2002/0095163 A1 | 7/2002 | Beyar | |
| 2002/0095181 A1 | 7/2002 | Beyar | |
| 2002/0128681 A1 | 9/2002 | Broome et al. | |
| 2002/0147382 A1 | 10/2002 | Neisz et al. | |
| 2002/0161382 A1 | 10/2002 | Neisz | |
| 2004/0193215 A1 | 9/2004 | Harari et al. | |
| 2004/0236373 A1 * | 11/2004 | Anspach, III | 606/232 |
| 2005/0004576 A1 | 1/2005 | Benderev | |
| 2005/0049634 A1 * | 3/2005 | Chopra | 606/213 |
| 2005/0199249 A1 | 9/2005 | Karram | |
| 2005/0256530 A1 | 11/2005 | Petros | |
| 2005/0277806 A1 | 12/2005 | Cristalli | |
| 2005/0283189 A1 | 12/2005 | Rosenblatt et al. | |
| 2006/0089525 A1 | 4/2006 | Mamo et al. | |
| 2006/0229493 A1 | 10/2006 | Weiser et al. | |
| 2006/0229596 A1 | 10/2006 | Weiser et al. | |
| 2006/0252980 A1 | 11/2006 | Arnal et al. | |
| 2006/0260618 A1 | 11/2006 | Hodroff et al. | |
| 2006/0282084 A1 * | 12/2006 | Blier et al. | 606/72 |
| 2007/0015953 A1 | 1/2007 | MacLean | |
| 2007/0078295 A1 | 4/2007 | Iandgrebe | |
| 2007/0173864 A1 | 7/2007 | Chu | |
| 2009/0012353 A1 | 1/2009 | Beyer | |
| 2009/0221868 A1 | 9/2009 | Evans | |
| 2010/0010631 A1 | 1/2010 | Otte et al. | |
| 2010/0094079 A1 | 4/2010 | Inman | |
| 2010/0168505 A1 | 7/2010 | Inman et al. | |
| 2010/0174134 A1 | 7/2010 | Anderson et al. | |
| 2010/0261952 A1 | 10/2010 | Montpetit et al. | |

FOREIGN PATENT DOCUMENTS

| | | |
|---|---|---|
| WO | WO9835606 A1 | 8/1998 |
| WO | WO9835616 A1 | 8/1998 |
| WO | WO9842261 A1 | 10/1998 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO9853746 A1 | 12/1999 |
| WO | WO0013601 A1 | 3/2000 |
| WO | WO0030556 A1 | 6/2000 |
| WO | WO0040158 A2 | 7/2000 |
| WO | WO0057796 A1 | 10/2000 |
| WO | WO0230293 A1 | 4/2002 |
| WO | WO02069781 | 9/2002 |
| WO | WO03034891 A2 | 5/2003 |
| WO | WO03034939 A1 | 5/2003 |

(56) References Cited

FOREIGN PATENT DOCUMENTS

| | | |
|---|---|---|
| WO | WO2006015031 A2 | 2/2006 |
| WO | WO2007002071 A1 | 1/2007 |
| WO | WO2007059199 A2 | 5/2007 |
| WO | WO2007097994 | 8/2007 |
| WO | WO2007137226 A2 | 11/2007 |
| WO | WO2007149348 A2 | 12/2007 |
| WO | WO2008057261 A2 | 5/2008 |
| WO | WO2009005714 A2 | 1/2009 |
| WO | WO2009017680 A2 | 2/2009 |

OTHER PUBLICATIONS

Mitek Brochure, Therapy of Urinary Stess Incontinence in Women Using Mitek GIII Anchors, by Valenzio C. Mascio, MD. (1993).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Vesica® Percutaneous Bladder Neck Stabilization Kit, A New Approach to Bladder Neck Suspenison, Microvasive® Boston Scientific Corporation, 4 pages (1995).

Precision Twist, Low Profile design for Precise Anchor Placement, Boston Scientific Microvasive, 2001 2 pp.

Vesica Sling Kit, Microvasive Boston Scientific, 1997, 6pp.

Precision Tack, The Precise Approach to Transvaginal Sling Procedures, Boston Scientific, 1998, 4pp.

\* cited by examiner

COLLAPSIBLE TISSUE ANCHOR DEVICE AND METHOD

PRIORITY

The present non-provisional application claims the benefit of U.S. provisional application No. 61/054,202 filed on May 19, 2008.

BACKGROUND OF THE INVENTION

1. Field of the Invention

The invention relates to apparatus and methods for treating pelvic conditions by use of anchored pelvic implants, mesh or sutures to support pelvic tissue. The pelvic conditions include conditions of the female or male anatomy, and specifically include treatments of female or male urinary and fecal incontinence, and treatment of female vaginal prolapse conditions including enterocele, rectocele, cystocele, vault prolapse, and any of these conditions in combination.

2. Background

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

One cause of urinary incontinence is damage to the urethral sphincter. Other causes include the loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence, and fistulas.

The female's natural support system for the urethra is a hammock-like supportive layer composed of endopelvic fascia, the anterior vaginal wall, and the arcus tendineus. Weakening and elongation of the pubourethral ligaments and the arcus tendineus fascia pelvis, and weakening of the endopelvic fascia and pubourethral prolapse of the anterior vaginal wall, may have a role in the loss of pelvic support for the urethra and a low non-anatomic position that leads to urinary incontinence.

In general, urinary continence is considered to be a function of urethral support and coaptation. For coaptation to successfully prevent or cure incontinence, the urethra must be supported and stabilized in its normal anatomic position. A number of surgical procedures and implantable medical devices have been developed over the years to provide urethral support and restore coaptation. Examples of such surgical instruments included Stamey needles, Raz needles, and Pereyra needles. See Stamey, Endoscopic Suspension of the Vesical Neck for Urinary Incontinence in Females, Ann. Surgery, pp. 465-471, October 1980; and Pereyra, A Simplified Surgical Procedure for the Correction of Stress Incontinence in Women, West. J. Surg., Obstetrics & Gynecology, pp. 243-246, July-August 1959.

One alternative surgical procedure is a pubovaginal sling procedure. A pubovaginal sling procedure is a surgical method involving the placement of a sling to stabilize or support the bladder neck or urethra. There are a variety of different sling procedures. Descriptions of different sling procedures are found in U.S. Pat. Nos. 5,112,344; 5,611,515; 5,842,478; 5,860,425; 5,899,909; 6,039,686; 6,042,534; and 6,110,101.

Some pubovaginal sling procedures extend a sling from the rectus fascia in the abdominal region to a position below the urethra and back again. The slings comprise a central portion that is adapted to support the urethra or a pelvic organ (i.e., a "support portion" or "tissue support portion"), and two extension portions bracketing the support portion, optionally a protective sheath or sheaths encasing at least the extension portions. Although complications associated with sling procedures are infrequent, they do occur. Complications include urethral obstruction, prolonged urinary retention, bladder perforations, damage to surrounding tissue, and sling erosion.

Other treatments involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced to the retropubic space. Peripheral or extension portions of the elongated urethral sling are affixed to bone or body tissue at or near the retropubic space. A central support portion of the elongated urethral sling extends under the urethral or bladder neck to provide a platform that compresses the urethral sphincter, limits urethral distention and pelvic drop, and thereby improves coaptation. Similar attached slings or supports have been proposed for restoring proper positioning of pelvic organs, e.g., the vagina or bladder.

Elongated "self-fixating" slings have also been introduced for implantation in the body, to treat pelvic conditions such as prolapse and incontinence conditions. Self-fixating slings do not require the extension portions to be physically attached to tissue or bone. Rather, the slings rely upon tissue ingrowth into sling pores to stabilize the sling. See, for example, commonly assigned U.S. Pat. Nos. 6,382,214, 6,641,524, 6,652,450, and 6,911,003, and publications and patents cited therein. The implantation of these implants involves the use of right and left hand sling implantation tools that create transvaginal, transobturator, supra-pubic, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the Bio-Arc® SP and SPARC® single use sling implantation tools sold in a kit with an elongated urethral sling by American Medical Systems, Inc.

In some sling implantation kits, the needle portion has a proximal straight portion extending from the handle and a distal curved portion terminating in a needle end or tip. As described in the above-referenced '003 patent, the kit may include more than one type of implantation tool (also, "insertion tool"). The kit may include one tool suitable for an outside-in (e.g. from the skin incision toward a vaginal incision) procedure and another that may be suitable for an inside-out (e.g. from the vaginal incision toward a skin incision) procedure. Surgeons that prefer an approach dictated by the surgeon's dominant hand can select the procedure and the appropriate implantation tool. Alternately, universal implantation tools (e.g., right and left sling implantation tools each suitable for both an inside-out and an outside-in approach) may be provided.

Optionally, a detachable protective sheath may encase some portion of an extension portion of a pelvic implant. Connectors may be attached to the ends of the extension portions for connecting with and end of an insertion tool. Generally speaking, the insertion tool ends are inserted axially into the connectors, and the extension portions of the implant are drawn through pathways trailing the connectors and needles to draw a central support portion against the pelvic tissue (e.g., the urethra) to provide support. The connectors are drawn out through skin incisions and the implant and encasing sheath are severed adjacent to the connectors.

Similar transobturator implantation procedures for implanting a pelvic implant to support a pelvic organ, e.g., the vagina, restored in proper anatomic position, are described in commonly assigned U.S. Patent Application Publication Nos. 2005/0043580 and 2005/0065395. Alternate implantation procedures for creating tissue pathways exiting the skin lateral to the anus and implanting an implant extending between the skin incisions to support a pelvic organ, e.g., the vagina, restored in proper anatomic position, are described in commonly assigned U.S. Patent Application Publication No. 2004/0039453 and in PCT Publication No. WO 03/096929. Various ways of attaching a sleeve end and implant mesh extension to a self-fixating tip are detailed in the above-referenced '450 patent, for example. Further ways of attaching extensions of an implant to an implantation tool are described in U.S. Patent Publication 2004/0087970. In each case extra incisions must be made in the patient's abdomen.

BRIEF SUMMARY OF THE INVENTION

The present patent application describes collapsible tissue anchor devices and methods for inserting into a tissue structure in a first non-collapsed configuration and then collapsing it into a second collapsed configuration. The disclosed tissue anchors may include a sleeve having an interior and a bolt or shank extending through it. The bolt or shank may include a head portion that engages an end of the sleeve. An end of the shank or the head portion itself may be exerted upon to apply a force to the sleeve causing it to move from a first generally tubular non-collapsed configuration to a second collapsed configuration. In the second collapsed configuration the sleeve has flanges that extend radially from the shank or bolt. The flanges act to prevent the anchor from being pulled out of the tissue. A sling, suture, mesh or the like may be coupled to a portion of the anchor to support tissue or an organ in order to treat incontinence, prolapse or any other conditions where a particular tissue or organ has moved from its typical anatomical location, thereby causing undesirable physiological symptoms.

The above summary of the invention is not intended to describe each illustrated embodiment or every implementation of the invention. The figures in the detailed description that follow more particularly exemplify these embodiments.

BRIEF DESCRIPTION OF THE DRAWINGS

The invention will be better understood when consideration is given to the following detailed description thereof. Such description makes reference to the annexed drawings wherein.

The preceding description of the drawings is provided for example purposes only and should not be considered limiting. The following detailed description is provided for more detailed examples of the invention. Other embodiments not disclosed or directly discussed are also considered to be within the scope and spirit of the invention. It is not the intention of the inventor to limit the scope of the invention by describing one or more example embodiments.

DESCRIPTION OF EXAMPLE EMBODIMENTS

The invention may be embodied in these and other specific forms without departing from the spirit or attributes thereof, and it is therefore desired that the embodiments be considered in all respects as illustrative and not restrictive, reference being made to the appended claims rather than to the foregoing description to indicate the scope of the invention.

Referring generally to FIGS. 1-31, various embodiments of the present invention are depicted showing soft tissue anchor devices. The anchor devices 10 can be advanced through soft tissue 12 that is positioned so that at least a limited space is available, or can be created, on both sides of the tissue (e.g., sacrospinous ligament, obturator internus muscle, etc.). As such, various anchor embodiments can extend through the tissue, with a first portion of the anchor provided on a first side of the tissue and a second portion of the anchor provided on a second side of the tissue. This configuration creates an anchor site adapted to secure or support implants, slings, mesh, and the like. The anchor devices described herein can be deployed and positioned within the pelvic region of a patent via a catheter or other delivery tool.

Figure 1:
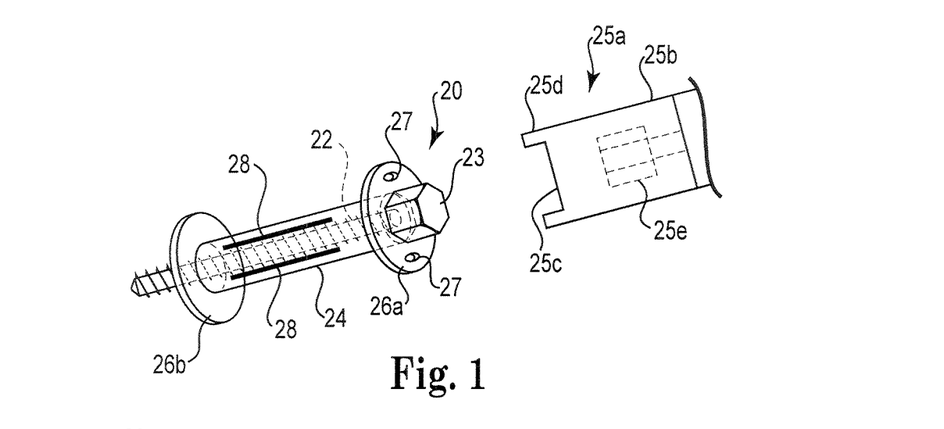
FIG. 1 is a perspective view of a bolt anchor device and corresponding driving tool.
Figure 2:
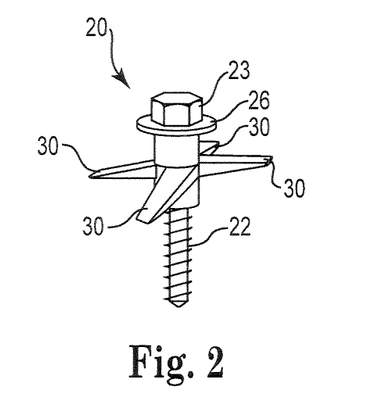
FIGS. 2-3 are perspective views of embodiments of a bolt anchor device.
Figure 3:
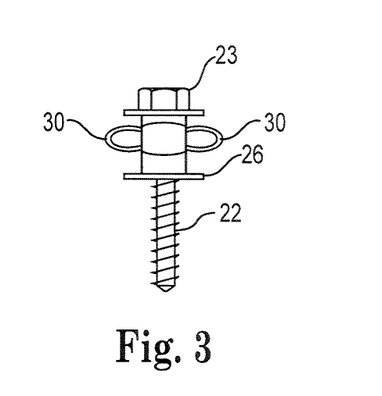

In the embodiments of FIGS. 1-3, the anchor comprises a bolt device or anchor 20 having a bolt 22, a tube or sleeve 24, and one or more washers 26 threadably engaged with the bolt 22. In FIG. 1, the bolt 22 is generally elongate and extends through the cylindrical tube 24 such that a first washer 26a is provided proximate a first end of the bolt 22 having a bolt head 23, and a second washer 26b is provided proximate a second end of the bolt 22. Further, the cylindrical tube 24 can include a plurality of longitudinal slots 28 defined therein. The slots 28 provide regions or lengths of weakness in the body of the cylindrical tube 24 that are vulnerable to longitudinal compression. As a result, while the tube 24 is generally elongate in its neutral or initial deployment state, a certain level of compression force on the tube 24 from the torque of turning the extending bolt 22 causes the tube 24 to collapse on itself along the weakened slot 28 regions. At the completion of the collapse, the previously elongate tube 24 is compressed to define a plurality of radially extending flanges 30.

A driver tool 25a can be utilized to deploy the bolt device 20 to and through the body tissue 12. Such a driver or actuator tool 25a can be manually and/or electrically powered and operated. The driver tool 25a may include a sleeve 25b having an open distal end 25c for receiving the bolt head 23. The end of the sleeve 25a may include one or more engagement members 25d that engage washer 26a. The engagement members 25d may comprise posts, shafts or rods that mate with openings or holes in washer 26a. A drive mechanism 25e can be operatively disposed in the sleeve 25a to engage and rotate bolt head 23. In one embodiment, washer 26a can include engagement apertures or features 27 adapted to receive a portion of the driver tool 20 such that the driver tool rotates the bolt 22 while keeping the washer 26a and concomitantly the tube 24 from rotating. By keeping the tube 24 and washer 26a stationary while rotating the bolt 22 a physician is able to collapse the tube 24 without needing any external forces against an outer surface of the tube 24 or without needing tissue engagement members or structures extending away from an outer surface of the tube 24 to engage surrounding tissue. Alternatively, a catheter, or other known delivery device can be used to deploy the bolt device 20 to the target tissue, wherein the actuator can then be used to drive the bolt device 20 through the tissue and into the securing configuration of a tissue anchor.

Various structures and techniques are envisioned for penetrating the tissue for positioning of the bolt device 20 through the tissue. For instance, the leading end of the bolt distal the bolt head 23 can include one or more angled members to aid in penetration through the tissue. In another embodiment of the invention either end or both ends of the bolt device 20 may be generally pointed to aid in delivery of the bolt device 20 to a particular tissue location. Alternatively, a drilling tool can be employed to bore through the tissue prior to insertion of the bolt device 20.

To facilitate anchoring within the tissue, the leading edge of the bolt device 20, including the washer 26b, may be inserted through the tissue for positioning on the second side of the tissue. The driver tool may then engage the bolt head 23 and engagement apertures 27. Actuation of the driver tool drives washer 26a and washer 26b toward each other, which in turn provides an increasing level of compression force on the still tube 24. As the compression forces increases with continued turning of the driver tool, the tube 24 begins to buckle due to the compromised structure created by the slots 28. As such, the tube 24 completely buckles to transform at least a portion of the tube 24 from its initial elongated deployment configuration to a compressed anchoring configuration. In the compressed anchoring configuration, the buckled tube 24 defines a plurality of flanges 30 extending radially from a central axis of the bolt 22 such that the body tissue is positioned intermediate washer 26b and the extended flanges 30, providing an anchor in the tissue. Further adjustments, e.g., loosening or tightening, can be made to the bolt head 23 via the driver tool 25a to stabilize and secure the anchor 20.

The bolt anchor 20 and its respective components can be constructed of known compatible metal or plastic materials. In addition, known support structures or devices, such as mesh, sutures and slings, can be selectively attached to one or more portions of the anchor 20, including the bolt head 23 or washer 26a, to provide a tissue anchor site for the support structures or devices. Any sutures or slings now known or to be developed can be connected to a portion of the bolt anchor 20. Additionally, multiple bolt anchors 20 may be used to suspend a suture or sling to support tissue or an organ.

Alternative embodiments of the bolt anchor 20 are depicted in FIGS. 2-3. The embodiment of FIG. 2 shows a bolt anchor 20 in its compressed state or configuration, with the anchor 20 having a single washer 26 threadably engaged with the bolt 22 proximate the bolt head 23. The embodiment of FIG. 3 includes a plurality of loop-shaped flanges 30. Components and structures of the bolt anchor 20 can take on a myriad of alternative shapes, sizes and configurations without deviating from the spirit and scope of the present invention.

Figure 4:
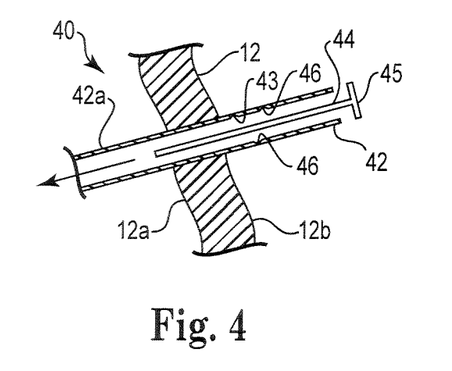
FIGS. 4-5 are partial section views of a sleeve anchor device, with weakened wall portions, inserted through and collapsed within target body tissue.
Figure 5:
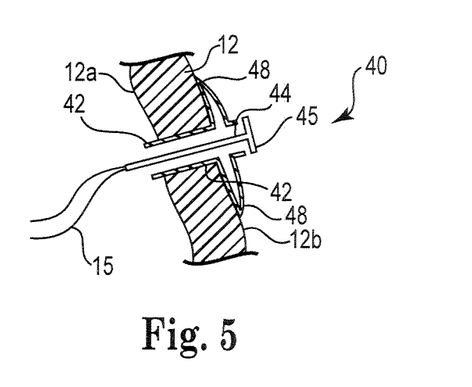

In another embodiment, as shown in FIGS. 4-5, the anchor 20 comprises a shank device 40 including an elongate sleeve 42 having a lumen 43 therethrough, and a shank 44 extendable through at least a portion of the lumen 43. The shank 44 includes a head portion 45 sized generally larger than the lumen 43 of the elongate sleeve 42. Further, the elongate sleeve 42 generally includes a plurality of compromised or weakened wall portions 46. The wall portions 46 can be formed or otherwise defined in the wall of the sleeve 42 with notches, scoring, folding, bending, decreased wall thickness, and the like.

In use, the sleeve 42 and shank head 45 are inserted through the tissue 12 to the second side of the tissue 12b such that at least a trailing end 42a of the sleeve 42 is positioned on the first side 12a of the tissue 12. The shank head 45 can be angled to aid in tissue penetration. Alternatively, a drilling or deployment tool can be employed to penetrate the tissue 12 to facilitate insertion of the anchor 20. After insertion of the shank head 45 and sleeve 42 through the tissue 12, the shank 44 and corresponding shank head 45 may be pulled back toward the tissue 12 to exert a compression force on the wall of the sleeve 42. This compression force causes the weakened wall portions 46 to bend or fold, causing the sleeve 42 to fold onto itself at the weakened wall portions 46 to form the anchor flanges 48 (FIG. 5). Various locking structures, configurations and techniques can be employed to aid in retaining the anchor 40 in the tissue 12, including any of the various locking features disclosed herein. For instance, FIGS. 15-18 illustrate a tabbed locking feature that can be implemented with the anchor 40. In certain embodiments, where continuous tension is applied to the suture 15 or shank 44, it may not be necessary to provide locking features.

As illustrated in FIGS. 6-14, various hinging anchor devices 50 generally include a main sleeve body portion 52 having an interior 54, and a shank 56 having a head portion 58. The main body portion 52 includes a plurality of adjacent longitudinal body sections 60 defined by separated longitudinal grooves or slots 61 in the body portion 52, with each of the sections 60 further including a living hinge 62. The living hinges 62 can be provided in the body sections 60 by predefined bends, scores, creases, pleats, folds, crimps, decreased wall thickness, and the like. Grooves or slots 61 of varying length, spacing, size and number can be included in the main body portion 52 to predefine the area of the main body portion 52 that is collapsible.

Figure 7:
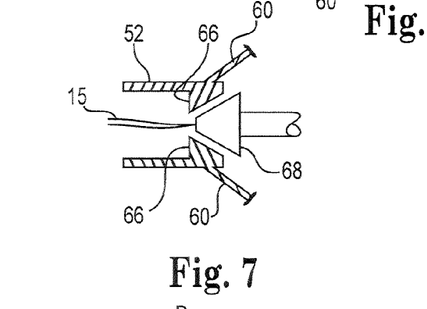
FIG. 7 is a partial section view of a lock feature for the sleeve anchor device.
Figure 8:
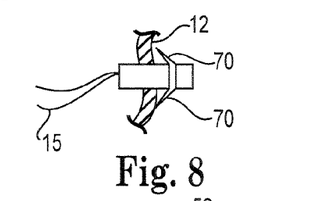
FIG. 8 is a partial cross section view of a collapsed anchor within target body tissue.
Figure 9:
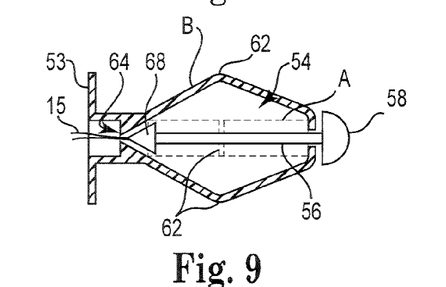
FIG. 9 is a side cross section view of a sleeve anchor device with living hinges, shown in a first deployment state and a partially collapsed state.
Figure 10:
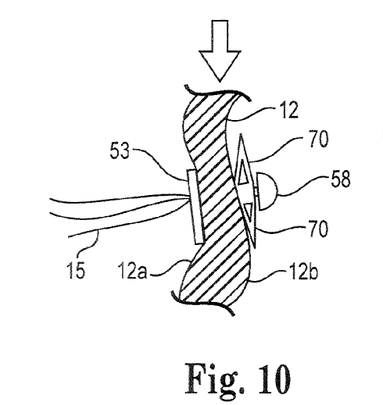
FIG. 10 is a side section view of the sleeve anchor device of FIG. 9 anchored within target body tissue.
Figure 11:
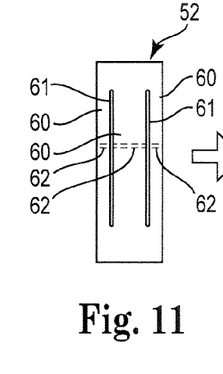
FIG. 11 is a side view of a sleeve for the sleeve anchor device, illustrating the position of the living hinges.
Figure 12:
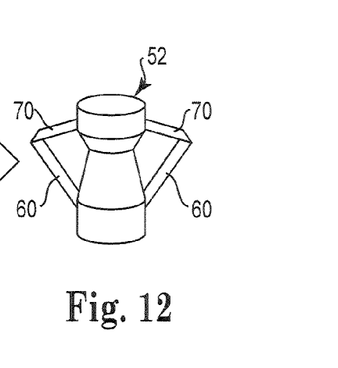
FIG. 12 is a view of the sleeve of FIG. 11 in a collapsed or anchoring state.
Figure 13:
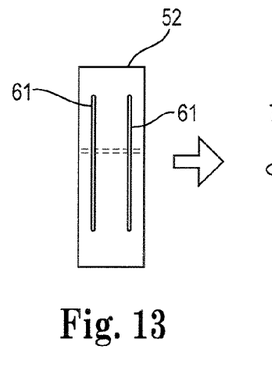
FIG. 13 is a side view of a sleeve for the sleeve anchor device, illustrating the position of the living hinges.
Figure 14:
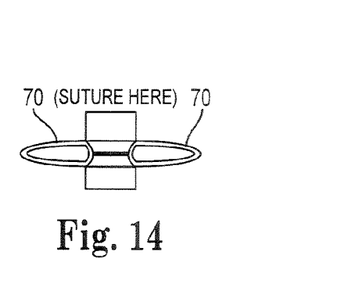
FIG. 14 is a top view of the sleeve of FIG. 13 in a collapsed or anchoring state.

The embodiment of FIGS. 7 and 9 further include a locking feature 64 within the interior 54 of the body portion 52. The locking feature 64 can include one or more tabs 66 extending into the interior 54. The tabs 66 are sized and shaped to mate with a corresponding end 68 (e.g., angled) of the shank 56 to lock the shank 56 in place within the body portion 52. In the embodiment of FIGS. 9-10, a washer or flange 53 can also be included at the end of the body portion 52 distal the shank head 58 to aid in retaining the anchor 50 within the tissue for those applications where the suture 15 is not continuously exerting a pulling force on the shank 56 or body portion 52. While a suture 15 is shown in the figures for connection with the anchor 50, other devices and structures, such as support mesh and slings, can be connected with the anchor 50 as well.

Figure 6:
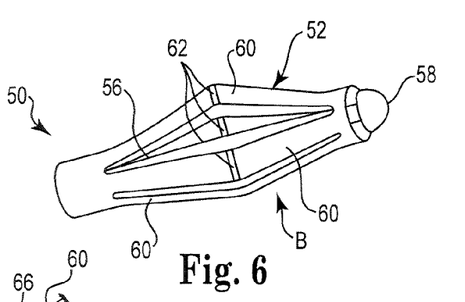
FIG. 6 is a perspective view of a sleeve anchor device with living hinges.

Like the embodiments of FIGS. 4-5, the hinging anchor 50 embodiment is inserted through the tissue 12 with the leading end including the shank head 58. In this elongate deployment state A (FIG. 9), a substantial portion of the body sections 60, including the living hinges 62, is disposed on the second side 12b of the tissue 12. The shank 56 is then pulled back toward the tissue 12 to exert a compression force on the body portion 52 that causes the body sections 60 to bend at the living hinges 62. This intermediate or partially collapsed state B for the main body portion 52 is illustrated in FIGS. 6 and 9. As a result of continued compression, the body sections 60 on the second tissue side 12b ultimately expand out to form extending flanges 70 to anchor the device 50 in place within the tissue 12. Again, washer 53 (FIGS. 9-10), locking feature 64 (FIGS. 7 and 9) and/or other structures or techniques can be employed to retain the anchor device 50 in its position within the body tissue 12.

FIGS. 11-14 illustrate various embodiments of the anchor device 50, wherein modifications in the positioning of the living hinges 62 results in extending flanges 70 of varying angles and designs.

Figure 15:
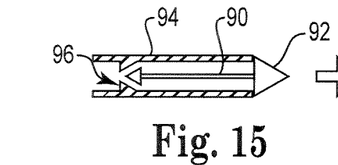
FIGS. 15-16 are side section views of a sleeve anchor device and a relatively long shank in an initial deployment state and a collapsed state.
Figure 16:
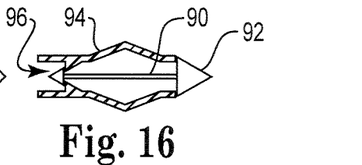
Figure 17:
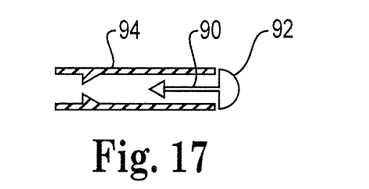
FIGS. 17-18 are side section views of a sleeve anchor device and a relatively short shank in an initial deployment state and a collapsed state.
Figure 18:
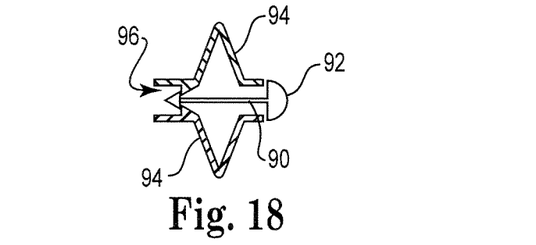

Referring to FIGS. 15-22, embodiments of the present invention employing slotted sleeves and shanks are depicted to illustrate the anchors in use, and alternative configurations for the shank and slot lengths. Any of these configurations can be employed, in whole or in part, with any of the anchor embodiments described or depicted herein. For instance, the shank 90 shown in FIGS. 15-16 can extend substantially the entire length of the collapsible sleeve 94 to create a travel distance for the shank 90 to the point of containment within the locking feature 96. This shorter travel distance, in turn, results in a reduced compression state for the sleeve 94 (FIG. 16). In contrast, a greater compression state is achieved with the embodiment of FIGS. 17-18, where the length of the shank 90 is substantially shorter than the length of the sleeve 94 to create a greater travel distance for the shank 90 to the locking feature 96. FIGS. 15-16 also show an embodiment of the shank head 92 angled to assist in penetrating body tissue during deployment.

Figure 19:
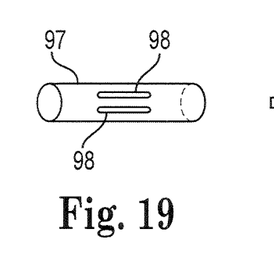
FIGS. 19-20 are perspective views of a sleeve anchor device, having relatively short longitudinal slots, in an initial deployment state and a collapsed state.
Figure 20:
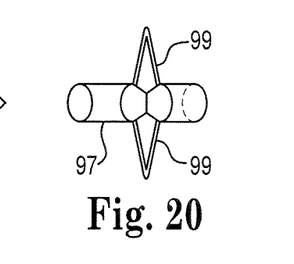
Figure 21:
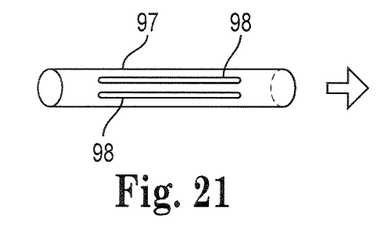
FIGS. 21-22 are perspective views of a sleeve anchor device, having relatively long longitudinal slots, in an initial deployment state and a collapsed state.
Figure 22:
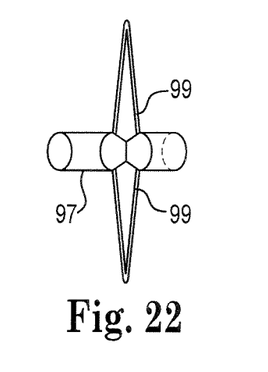

FIGS. 19-21 illustrate embodiments of the anchor device with alternative slot 98 lengths along the collapsible sleeve 97. Relatively short slots 98 (FIGS. 19-20) in the sleeve 97 results in shorter extending flanges 99 in a fully collapsed state (FIG. 20). In contrast, relatively long slots 98 (FIGS. 21-22) results in longer extending flanges 99 in the fully collapsed state. Similarly, shorter slots 98 dictate a shorter travel distance for the shank 90 to actuate complete collapse of the sleeve 97, while longer slots 98 dictate a longer travel distance for the shank 90 to actuate complete collapse.

Figures 23, 24, 25, 26:
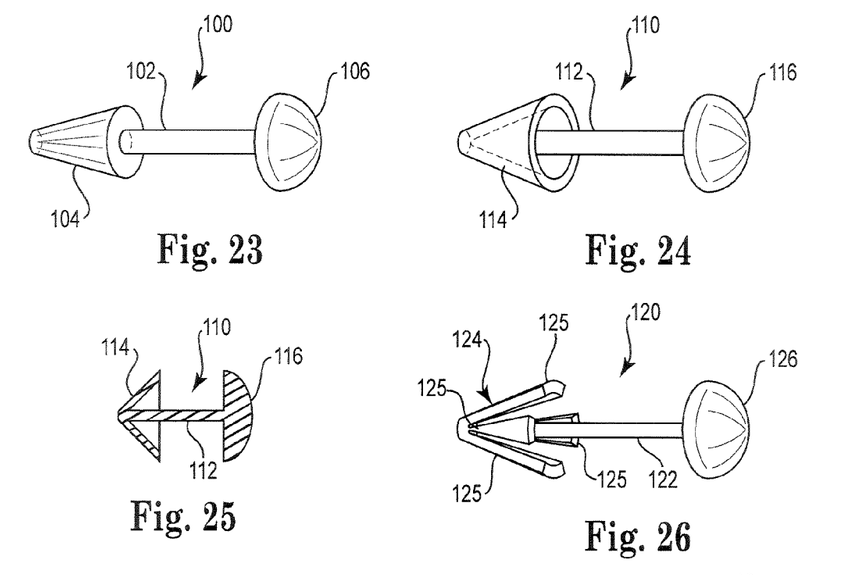
FIGS. 23-26 are views of various embodiments of the shank for use in embodiments of the sleeve anchor device.

FIGS. 23-26 illustrate potential embodiments for the shank member capable of implementation with various anchors of the present invention. The shank 100 of FIG. 23 can comprise a central shaft portion 102 extending between a head portion 106 and a travel end 104 adapted to traverse the interior of the collapsible sleeve. The head portion 106 can be rounded, or angled (e.g., FIGS. 15-16) to facilitate tissue penetration during deployment. The travel end 104 in this embodiment can be angled and rigid (e.g., generally solid) to promote engagement of the travel end 104 within a locking feature of the anchor (e.g., feature 96 of FIG. 16). Alternatively, the shanks 110, 120 of FIGS. 24 and 26 can include flexible, or otherwise deformable or malleable, travel ends 114, 124. In the embodiment of FIG. 24, the flexible travel end 114 extends from the shaft 112, distal the head portion 116, and is configured with a generally open or hollow interior (FIG. 25). As such, the flexible travel end 114 is capable of selectively deforming within the collapsible sleeve and upon engagement with locking features, washers, and other structures or components associated with the disclosed anchor devices. Similarly, the flexible travel end 124 of shank 120 in the embodiment of FIG. 26 includes a plurality of angled members 125 adapted for selective deformability during travel and engagement. The flexible travel end 124 is positioned on an end of the shaft 122, distal the head portion 126.

Figure 27:
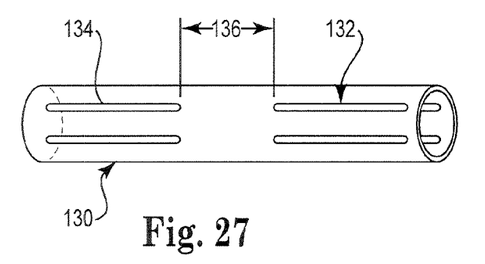
FIGS. 27-28 are views of a sleeve anchor device having multiple collapsing regions, in an initial deployment state and in a collapsed state anchoring the device in a target tissue location.
Figure 28:
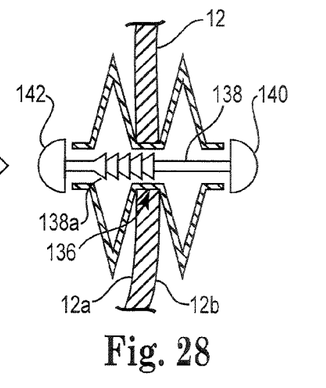
Figure 29:
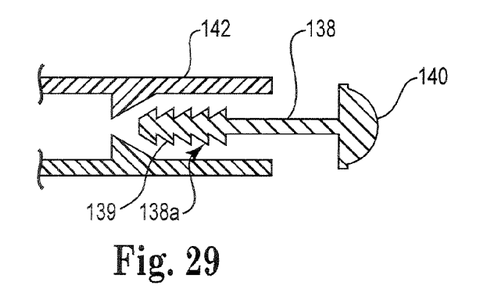
FIG. 29 is a partial side section view of an engagement or locking feature for the sleeve anchor device of FIG. 28.

As illustrated in FIGS. 27-29, embodiments of the present invention can include a collapsible sleeve 130 having multiple slotted portions 132, 134 longitudinally spaced from one another. As such, collapsible sleeve 130 includes two distinct collapsible regions separated by an intermediate body portion 136. The sleeve 130, in its initial elongate deployment state (FIG. 27), is inserted or penetrated through body tissue 12 such that the slots 132 of the first collapsible region are positioned on a second tissue side 12b, with the slots 134 of the second collapsible region positioned on the first second tissue side 12a. Upon deployment, the shank 138 is pulled back, whereby the head portion 140 engages the sleeve 130 to apply a compression force on the sleeve 130. To facilitate corresponding compression force on the compression slots 134 residing on first tissue side 12a, an end cap 142 can be provided and adapted for engagement with travel end 138a of the shank 138. Travel end 138a can include indexing teeth 139 spaced and configured to provide stepped or incremental engagement with corresponding structures or features in the end cap 142. Other connection features and techniques are envisioned to selectively couple the shank 138, or the travel end 138a, with the second compression region having slots 134 defined therein.

Figures 30, 31:
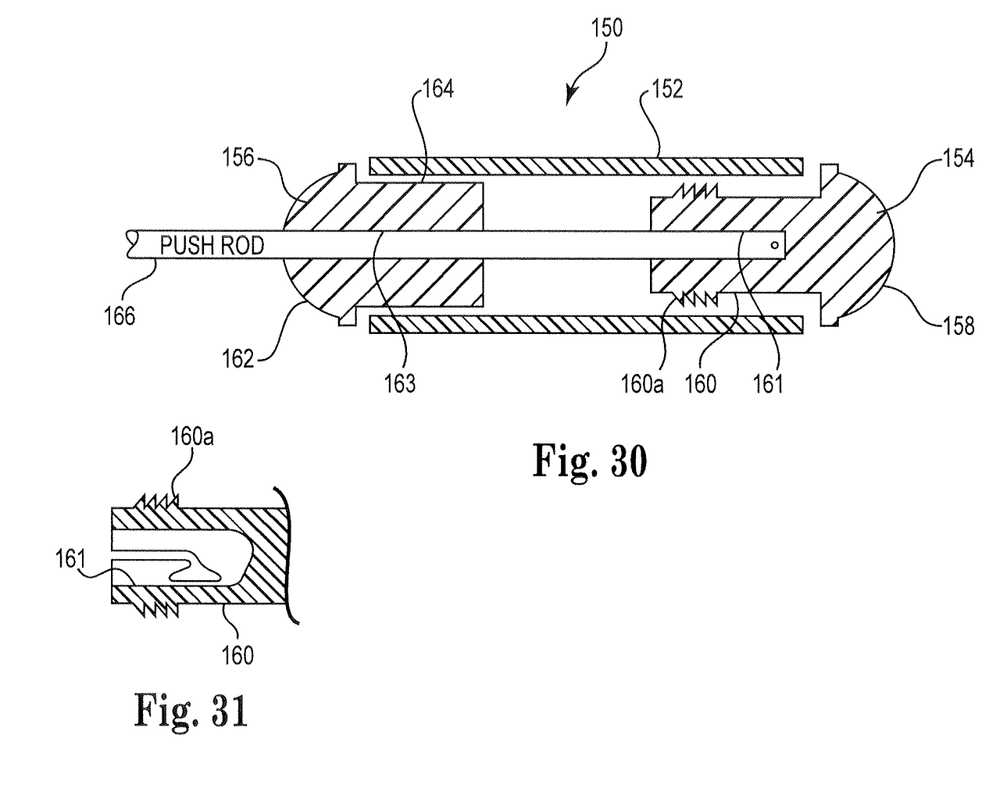
FIG. 30 is a side section view of a sleeve anchor device having opposing end cap members and an engageable push rod.
FIG. 31 is a partial section view of an end cap member and an end portion of the push rod of FIG. 30.

As illustrated in FIGS. 30-31, an anchor device 150 of the present invention can include a sleeve portion 152, a first cap member 154 and a second cap member 156, with the cap members 154, 156 being insertable within respective ends of the sleeve 152. Cap member 154 includes a head portion 158 abuttable against an outside portion of the sleeve 152, such that an interior cap portion 160 extends into the lumen of the sleeve 152. The interior cap portion 160 can further include a recess or bore 161 extending a distance therein. Cap member 156 includes a head portion 162 abuttable against an outside portion of the sleeve 152, with an interior cap portion 160 extending into the lumen of the sleeve 152. The interior portion 160 of cap member 154 can include teeth 160a, or other engagement features, for interfacing and locking into corresponding features provided with the interior cap portion 164 of cap member 156. The cap member 156 can include a bore 163 in alignable communication with the interior of the sleeve and the recess 161 in cap member 154.

An engagement or push rod 166 is sized and shaped for insertion through the bore 163 of cap member 156, through the sleeve 152 and into the recess 161 of cap member 154, as shown in FIG. 30. The recess 161 can be configured and shaped to receive a leading end of the push rod 166, as shown in FIG. 31. Once it is positioned within the recess 161, the push rod 166 can be turned into a locking position, press fit, or otherwise engaged with the cap member 154 via the recess 161. Upon engagement, the push rod 166 can be pulled which, in turn, pulls cap member 154 against the sleeve 152 to exert a compression force on the sleeve 152 between the two cap members 154, 156. The various weakened wall and hinging features described herein for various embodiments can be included along a length or portion of the sleeve 152 to facilitate collapse of the sleeve 152. As with the other embodiments, this collapse provides an anchoring device within the body tissue 12 that can be connected with sutures, slings, mesh and like devices.

The invention described and depicted herein may be embodied in these and other specific forms without departing from the spirit or attributes thereof, and it is therefore desired that the embodiments be considered in all respects as illustrative and not restrictive, reference being made to the appended claims rather than to the foregoing description to indicate the scope of the invention.

What is claimed is:

1. A collapsible tissue anchor device, comprising:
a generally tubular sleeve having a distal insertion portion and a lumen extending therethrough, at least one wall portion adapted to provide a collapsing region for the sleeve, and at least one internal tab extending within the lumen and having an angled surface, with distal insertion portion of the sleeve insertable through tissue in a non-collapsed state; and
an elongate member having at least one distal head portion and an opposing end portion having at least one tapered flange distal the at least one head portion, with a suture member attached to and extending from the at least one tapered flange of the elongate member, the elongate member adapted for insertion and traversal through at least a portion of the lumen, whereby force exerted by the at least one distal head portion on an outside portion of the sleeve causes the sleeve to collapse around the collapsing region such that the distal insertion portion is collapsed on a side of the tissue to angle down away from the at least one head portion of the elongate member toward the at least one tapered flange such that tips of the insertion portion engage the tissue and restrict pullout, with the at least one tapered flange adapted to travel along the angled surface of the at least one internal tab until the tapered flange securely engages with the at least one internal tab of the sleeve to limit transversal of the elongate member.

2. The device of claim 1, wherein the at least one internal tab includes two opposing internal tabs.

3. The device of claim 1, wherein the sleeve further includes a plurality of longitudinal slots.

4. The device of claim 1, wherein the collapsing region includes one or more living hinges along a portion of the sleeve.

5. The device of claim 1, wherein the collapsing region includes one or more weakened wall portions along a portion of the sleeve.

6. The device of claim 1, wherein the sleeve is generally elongate for deployment into body tissue of a patient.

7. The device of claim 1, wherein the suture member is connectable with a mesh or a sling.

8. The device of claim 1, wherein at least a portion of the head portion of the elongate member is angled to facilitate penetration through body tissue.

9. A collapsible tissue anchor device, comprising:
a general tubular sleeve having a lumen extending therethrough, the sleeve having;
a distal insertion portion adapted for insertion through tissue in a non-collapsed state;
a plurality of slots provided along a longitudinal length of the sleeve to define a plurality of sleeve segments;
a living hinge defined across the plurality of sleeve segments;
at least one internal tab extending within the lumen; and
an elongate member having at least one distal head portion and a generally arrow-shaped end portion distal the at least one head portion and adapted for insertion and traversal through at least a portion of the lumen, with a filament member attached to and extending from the generally arrow-shaped end portion, whereby force exerted by the head portion on an outside portion of the sleeve causes the sleeve to collapse around the living hinges such that the distal insertion portion is collapsed on a side of the tissue to angle down away from the at least one head portion of the elongate member toward the generally arrow-shaped end portion, such that tips of the collapsed distal insertion portion engage the tissue to restrict pullout, with the generally arrow-shaped end portion adapted to securely engage with the at least one internal tab of the sleeve to limit transversal of the elongate member.

10. The device of claim 9, wherein the at least one internal tab includes two opposing internal tabs.

11. The device of claim 9, wherein the plurality of slots includes two spaced groupings of slots to define two collapsible regions for the sleeve.

12. The device of claim 9, wherein the sleeve is generally elongate for deployment into body tissue of a patient.

13. The device of claim 9, wherein the filament member is connectable with the a mesh or a sling.

14. The device of claim 9, wherein at least a portion of the head portion of the elongate member is angled to facilitate penetration through body tissue.

\* \* \* \* \*